United States Patent [19]
Khan et al.

[11] Patent Number: 6,017,901
[45] Date of Patent: Jan. 25, 2000

[54] HEAVY METAL SALTS OF SUCCINIC ACID HEMIESTERS WITH HYALURONIC ACID OR HYALURONIC ACID ESTERS, A PROCESS FOR THEIR PREPARATION AND RELATIVE PHARMACEUTICAL COMPOSITIONS

[75] Inventors: Riaz Khan, Sonning; Paul A. Konowicz, Farnham, both of United Kingdom; Antonella Flaibani, Udine; Valentina Gombac, Trieste, both of Italy

[73] Assignee: Fidia Advanced Bioplymers S.r.L., Brindisi, Italy

[21] Appl. No.: 08/966,636

[22] Filed: Nov. 10, 1997

Related U.S. Application Data

[63] Continuation-in-part of application No. PCT/EP96/01979, May 8, 1996.

[51] Int. Cl.⁷ ............................. A61K 31/73; C08B 37/00
[52] U.S. Cl. ............................. 514/54; 536/53; 536/55.3; 424/1.73; 424/9.35; 424/9.43
[58] Field of Search ...................... 536/53, 55.3; 514/54; 424/1.73, 9.35, 9.43

[56] References Cited

U.S. PATENT DOCUMENTS

| | | | |
|---|---|---|---|
| 4,746,504 | 5/1988 | Nimrod et al. | 424/1.1 |
| 4,851,521 | 7/1989 | della Valle et al. | 536/55.1 |
| 5,688,931 | 11/1997 | Nogusa et al. | 536/20 |

FOREIGN PATENT DOCUMENTS

| | | |
|---|---|---|
| 0066283 | 12/1982 | European Pat. Off. . |
| 0314835 | 5/1989 | European Pat. Off. . |

OTHER PUBLICATIONS

Liesegang, *Survey of Opthalmology*, "Viscoelastic Substances in Opthalmology", vol. 34, No. 4 (Jan. 1990–Feb. 1990).

Milanino et al., "Copper and Zinc in Inflammation", *Inflammation and Drug Therapy Series, vol. IV, 1989*. Month not available.

Database WPI Derwent, Japan A 54 036 388, Mar. 17, 1979.

*Primary Examiner*—Kathleen K. Fonda
*Attorney, Agent, or Firm*—Abelman, Frayne & Schwab

[57] ABSTRACT

Hyaluronic acid or hyaluronic acid ester derivatives, wherein one or more hydroxy functions of its 1,4β-D-glucuronic acid and 1,3-β-N-acetyl-D-glucosamine alternating repeating units are esterified with a carboxyl group of succinic acid to form the succinic hemiester of hyaluronic acid or hyaluronic acid esters. These derivatives are used to prepare the corresponding heavy metal salts of succinic hemiesters of hyaluronic acid or with hyaluronic acid partial or total esters. These salts are used as active ingredients in the preparation of pharmaceutical compositions to be used as antibacterial and disinfectant agents for the treatment of wounds, burns and ophthalmia or as antiinflammatory agents in particular for the preparation of pharmaceutical compositions for the treatment of osteoarticular disorders.

37 Claims, No Drawings

HEAVY METAL SALTS OF SUCCINIC ACID HEMIESTERS WITH HYALURONIC ACID OR HYALURONIC ACID ESTERS, A PROCESS FOR THEIR PREPARATION AND RELATIVE PHARMACEUTICAL COMPOSITIONS

CROSS-REFERENCE TO RELATED APPLICATIONS

This application is a Continuation-in-Part of PCT Application No. PCT/EP96/01979, filed on May 8, 1996.

FIELD OF THE INVENTION

The present invention relates to succinic acid hemiesters with hyaluronic acid or with hyaluronic acid partial or total esters, and heavy metal salts of said succinic hemiesters with hyaluronic acid or hyaluronic acid total or partial esters, a process for their preparation and pharmaceutical compositions containing these salts as active ingredients.

BACKGROUND OF THE INVENTION

Hyaluronic acid is a polysaccharide whose chain is constituted by alternating units of 1,4-β-D-glucuronic acid and 1,3-β-N-acetyl-D-glucosamine. Hyaluronic acid is a fundamental component of connective tissue of animals, being present, for example, in the skin and cartilage. It is also found in high concentrations in the umbilical cord, in the synovial fluid and vitreous humor of the eye. Currently, the preferred source of hyaluronic acid is by extraction from cockscombs, even though the production of hyaluronic acid from Streptococcus cultures is becoming increasingly widespread (T. J. Lieselang. Survey of Ophthalmology 34,268–293, 1990).

As hyaluronic acid is a fundamental component of the connective tissue, it is biocompatible, bioadsorbable and not immunogenic. It therefore plays a key role in many biological functions, such as tissue hydration, the organization of proteoglycans in the cartilage, tissue repair, embryonic development and lubrication and protection of joint cartilage. This polysaccharide is commonly used in the treatment of some joint diseases, such as rheumatoid arthritis. It is also used in what is known as microviscosurgery, and in particular, in surgery to the eye. In this application, the biocompatibility and rheological characteristics of concentrated solutions of high-molecular-weight hyaluronic acid are exploited.

In cases of inflammation of the joints, hyaluronic acid is degraded by superoxide radicals (Greenwald R. A. et al., Inflammation, 10, 15–30, 1986). This degradation determines a notable reduction in the rheological and viscoelastic characteristics of the synovial fluid, markedly reducing the lubricant and protective effect which hyaluronic acid has on the cartilage. It has been hypothesized that the superoxide dismutase enzyme constitutes the main defense against damage caused by the superoxide radical which is produced in the course of inflammatory processes. Copper and zinc are components of the superoxide dismutase enzyme, the function of which seems to be to protect cells from the toxic effects of endogenous superoxide radicals.

Rheumatoid arthritis has been associated with zinc deficiencies and an antiinflammatory activity has been hypothesized for zinc itself (A. Frigo et al., "Copper and Zinc in Inflammation", Inflammation and drug therapy series, Vol. IV, Kluwer Academic Publishers, pp. 133–142, 1989). Treatment with zinc sulfate has proved to be efficacious in controlling joint disorders caused by arthritis in patients affected by psoriasis.

In the same way, alterations in copper concentrations have been observed in patients affected by inflammatory diseases in the joints (C. W. Denko, "Copper and Zinc in Inflammation, Inflammation and drug therapy series, Vol. IV, Kluwer Academic Publishers, pp. 1–5, 1989). Copper-based compounds have been used to treat rheumatoid arthritis and their activity is attributed to copper ions.

Gold salts are also used as drugs to treat arthritis, together with known antiinflammatory products of a steroid and non-steroid type (U.S. Pat. No. 4,746,504).

Many silver salts, such as silver fluoride, silver iodide, silver lactate, have been used as antibacterial agents for topical use. Their antimicrobial activity is due to the action of the Ag+ ions.

Heavy metal salts of hyaluronic acid are therefore already known to the state of the art, such as silver, gold, cerium and tungsten. The reaction between a sodium hyaluronate aqueous solution and a silver nitrate solution gives the silver salt of hyaluronic acid. Pharmaceutical preparations containing all these compounds are used to advantage for the treatment of burns, wounds and some ophthalmic infections such as gonococcus-induced conjunctivitis (A. Nimrod and B. Greenman, U.S. Pat. No. 4,746,504, May 24, 1988).

However, neither hyaluronic acid nor hyaluronic acid partial or total ester derivatives wherein one or more hydroxy functions of its 1,4β-D-glucuronic acid and 1,3-β-N-acetyl-D-glucosamine alternating repeating units esterified with a carboxyl group of succinic acid to form the succinic hemiester of hyaluronic acid or hyaluronic acid total or partial esters are known to the state of the art.

SUMMARY OF THE INVENTION

The present invention concerns a succinic hemiester of hyaluronic acid or of a hyaluronic acid total or partial ester and its inorganic salt with a heavy metal.

In particular the succinic acid hemiester with hyaluronic acid, or with a hyaluronic acid total or partial ester is characterized by having the following repeating unit (I):

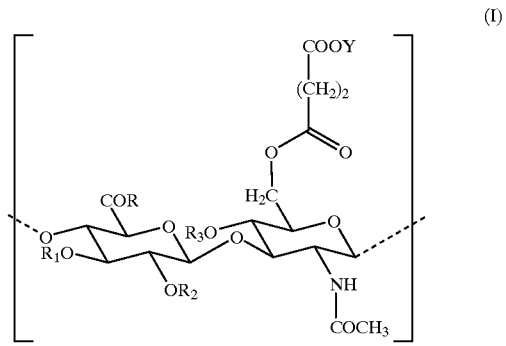

wherein $R_1$, $R_2$ and $R_3$ equal or different from each other are H or CO—$(CH_2)_2$—COOY, wherein Y is H, R is OH, or an alcoholic residue.

The hyaluronic acid esters contemplated for preparing the succinic acid hemiester are the total or partial ester with alcohol of the aliphatic or cycloaliphatic series, which do not themselves possess a notable pharmacological action disclosed in U.S. Pat. No. 4,851,521, which we incorporate herewith by reference.

The heavy metal salt of the succinic acid hemiester with hyaluronic acid or with a hyaluronic acid total or partial ester are in particular characterized by having the following repeating unit (II):

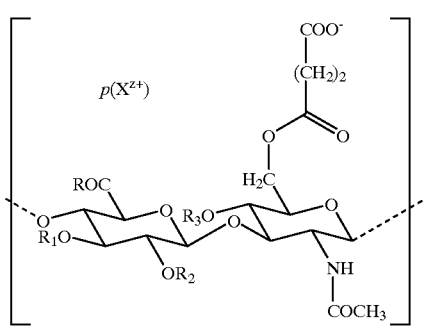

(II)

wherein $R_1$, $R_2$ and $R_3$ equal or different from each other are H or CO—$(CH_2)_2$—COO⁻, R is O⁻, or an alcoholic residue, ($X^{z+}$) is a cation of a heavy metal in which z is a number comprised between 1 and 6, p is an integer or a decimal number, comprised between 0.1 and 5 provided that $p(X^{z+})$ is equal to the number of anionic groups COO⁻ present in said repeating unit. The heavy metal salts according to the present invention are characterized by having a far greater negative charge density than the corresponding heavy metal salt of the starting hyaluronate. Indeed, the new substituting group, i.e. succinic acid, can bind, theoretically, to all the alcoholic functions of the repeating unit, giving a polysaccharide containing up to four succinic groups per repeating unit and therefore four more negative charges available for the formation of salts.

A further subject of the present invention relates to the process for preparing said succinic acid hemiester with hyaluronic acid or with a hyaluronic acid partial ester and the corresponding heavy metal salt.

This process in particular comprises the following steps:
a) converting the hyaluronic acid sodium salt into a salt selected from the group consisting of pyridinium, tetraalkylammonium, tetraarylammonium, tetraalkylphosphonium, tetraarylphosphonium salt, in the presence of water and an aprotic solvent,
b) treating the solution coming from step (a) with succinic anhydride in the presence of an organic base, as the catalyst, removing the pyridinium tetraalkylammonium, tetraarylammonium, tetraalkylphosphonium, or tetraarylphosphonium cation by dialysis, thereby obtaining the succinic acid hemiester having the repeating unit (I) provided that at least one of said repeating units (I) has R=OH, and optionally recovering the obtained product by freeze-drying,
c) treating the solution directly coming from the preceding step or an aqueous solution of the recovered solid product coming from the preceding step with an aqueous solution of an inorganic salt of the heavy metal, and recovering the product by filtration and vacuum drying.

In case of the preparation of the heavy metal salt with the succinate hemiester of the total ester of hyaluronic acid, the process according to the present invention contemplates the following steps:
b') treating the hyaluronic acid ester dissolved or suspended in a mixture of water and an aprotic solvent with succinic anhydride in the presence of an organic base, as the catalyst, thereby obtaining the succinic acid hemiester having the repeating units (I) wherein R is a residue of an alcohol, and optionally recovering the obtained product by freeze-drying, c') treating the solution directly coming from the preceding step or an aqueous solution of the recovered solid product coming from the preceding step with an aqueous solution of an inorganic salt of the heavy metal, and recovering the product by filtration and vacuum drying.

The heavy metal salts of succinic acid hemiester with a hyaluronic acid or with a partial or total hyaluronic acid ester according to the present invention can be used to advantage as antimicrobial, antibacterial and disinfectant agents, for the treatment of wounds, burns and ophthalmia, or they can be incorporated in suitable pharmaceutical forms, optionally in association with one or more other pharmacologically active substances, having a similar therapeutic activity.

In addition they can be advantageously used as disinfectant agents, not only for the preparation of drugs, but also as active ingredients for the preparation of the so-called health care products, such as cosmetic creams and ointments, shave and after shave lotions and hair lotions etc. or biomaterials such as membranes non-woven tissues, gauzes, etc.

The heavy metal salts of succinyl monoesters of hyaluronic acid can be also advantageously used as antiinflammatory agents in the treatment of arthritis and inflammations affecting the joints optionally in association with other pharmaceutically active principles having a similar therapeutical activity.

DETAILED DESCRIPTION OF THE INVENTION

The term "heavy metal" encompasses any pharmaceutically active metal in the 4, 5 or 6 period of the periodic table.

The preferred heavy metal salts according to the present invention are those whose cation is: zinc, silver, copper, gold, iron, cerium and tungsten salts of succinic derivatives of hyaluronic acid.

It has in fact been found that compared with the corresponding salts with hyaluronic acid or with hyaluronic acid partial esters these salts offer an advantage over the already-known products containing heavy metal salts, because the salts according to the present invention can bind a high number of heavy metal cations. Indeed, while hyaluronic acid can bind only one counter-ion per repeating unit, the salts according to the present invention bind at least twice as many counter-ions per repeating unit.

It is therefore advantageous to use these heavy metal salts with higher concentrations of metal for the therapeutic applications identified and described in the text, as this is the most active component in the preparation.

Hyaluronic acid or hyaluronic acid esters of any molecular weight can be used to prepare succinyl derivatives thereof. In the present invention, samples of hyaluronic acid with a molecular weight of between 30,000 and 760,000 Daltons were used, but this range is not critical for the purpose of the present invention.

Preferred succinic acid hemiesters of hyaluronic acid or hyaluronic acid esters are those having in the repeating unit (I) $R_1=R_2=R_3=H$ and the corresponding heavy metal salts wherein in the repeating unit (II) X is selected from the group consisting of: silver, gold, copper, zinc, z is comprised between 1 and 3 and p is comprised between 0.3 and 2.

Another class of preferred succinic acid hemiesters with hyaluronic acid or hyaluronic acid esters are those having at least one repeating unit (I) wherein $R_1=R_3=H$ and $R_2=CO—(CH_2)_2—COOY$ and at least one repeating unit (I), wherein $R_2=R_3=H$, and $R_1=CO—(CH_2)_2—COOY$ has the above mentioned meanings and the corresponding heavy metal salts have at least one repeating unit (II)

wherein $R_1=R_3=H$ and $R_2=CO-(CH_2)_2-COO^{31}$ and at least one repeating unit (II) wherein $R_2=R_3=H$, $R_1=CO-(CH_2)_2-COO^-$, X is selected from the group consisting of: silver, gold, copper, zinc, iron, z is comprised between 1 and 3 and p is comprised between 0.6 and 3.

In the process according to the present invention for preparing the succinic acid hemiesters with hyaluronic acid or with hyaluronic acid partial esters, in step (a) the hyaluronic acid is preferably converted to the corresponding pyridinium salt. In particular this conversion encompasses a previous dissolution of the hyaluronate sodium salt in a mixture of water and dimethylformamide, a treatment with a cationic exchange resin for obtaining the corresponding free hyaluronic acid. After removal of the resin the solution is neutralized with pyridine and the pyridinium salt is thus obtained.

In step (b) or (b') of both processes the amount of succinic anhydride is not critical, although it is preferable to add high excess with respect to hyaluronic acid. In fact the best results are obtained when the molar ratio of succinic anhydride /free OH groups present in the repeating unit (III)

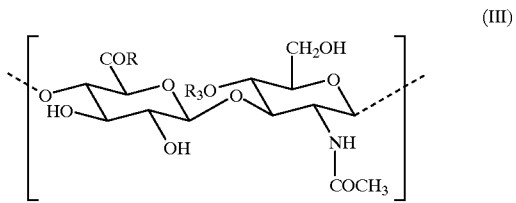

(III)

wherein R has the above mentioned meanings, of the starting hyaluronic acid or hyaluronic acid partial ester, ranges between 15 and 90. Although the temperature is not critical, the best results are obtained if step (b) or (b') of both processes is carried out at 70° C. The preferred organic base used as catalyst in step (b) or (b') of both processes is selected from the group consisting of 4-dimethylaminopyridine, pyridine, or mixtures thereof. By using large amounts of 4-dimethylamminopyridine a succinic acid hemiester with hyaluronic acid or a hyaluronic acid ester with a high degree of succinylation is obtained, by using pyridine alone or in admixture with small quantities of 4-dimethylaminopyridine a succinic acid hemiester with hyaluronic acid with a low degree of succinylation is obtained. Anyway the stronger the reaction conditions, such as temperature, reaction times etc., the greater the degree of esterification of the derivatives formed.

For the preparation of the Ag salt of the succinate hemiester with hyaluronic acid or a hyaluronic acid ester, in step (c) or (c') the succinic acid hemiester with hyaluronic acid or the succinic acid hemiester with hyaluronic acid ester is preferably treated with an aqueous solution of silver nitrate to form the silver salt of succinate hemiester with hyaluronic acid or hyaluronic acid ester. The Ag salt according to the present invention precipitates from the solution and is recovered by filtration or centrifugation. The precipitate is then washed with ethanol and vacuum dried at 40° C.

The silver compounds of the succinyl derivatives are prepared in the complete dark. All the operations to prepare the silver nitrate solutions, and to prepare the succinyl silver hyaluronate were performed in the dark and the resulting products were stored away from sources of light.

For the preparation of the Cu salts of the succinate hemiester with hyaluronic acid or a hyaluronic acid ester, in step (c) or (c') of both processes, the succinic acid hemiester with hyaluronic acid or the succinic acid hemiester with hyaluronic acid ester is preferably treated with an aqueous solution of $CuCl_2$ to form the Cu salt of succinate hemiester with hyaluronic acid or with the hyaluronic acid ester.

For the preparation of the Zn salts of the succinate hemiester with hyaluronic acid or a hyaluronic acid ester, in step (c) or (c') of both processes the succinic acid hemiester with hyaluronic acid or the succinic acid hemiester with hyaluronic acid ester is preferably treated with an aqueous solution of $ZnCl_2$ to form the Zn salts of the succinate hemiester with hyaluronic acid or with the hyaluronic acid ester.

For the preparation of the Au salts of the succinate hemiester with hyaluronic acid or a hyaluronic acid ester, in step (c) or (c') of both processes the succinic acid hemiester with hyaluronic acid or the succinic acid hemiester with hyaluronic acid ester is preferably treated with an aqueous solution of $HAuCl_4$ to form the Au salts of the succinate hemiester with hyaluronic acid or with the hyaluronic acid ester. For the preparation of the iron salts of the succinate hemiester with hyaluronic acid or a hyaluronic acid ester in step (c) or (c') or both processes the succinic acid hemiester with hyaluronic acid or with a hyaluronic acid ester is preferably treated with an aqueous solution of $FeCl_2$.

The pharmaceutical compositions according to the present invention to be used for the treatment of burns, wounds and ophthalmia preferably contain the Ag salt according to the present invention and are moreover in the form of ointments, creams gels.

The pharmaceutical compositions to be used for the treatment of osteoarticular diseases preferably contain Au, Zn, Cu salts or mixtures thereof.

The iron salts of succinate hemiester with hyaluronic acid or with a hyaluronic acid ester are used for preventing post surgical adhesions in the form of suitable therapeutical compositions or as biomaterial. We report hereafter some specific examples for the preparation of O-succinylhyaluronates and relative heavy metal salts, but any variation not specifically reported in the following examples is to be considered as coming within the scope of the present invention. The heavy metal salts having the repeting units of formula (II) as such or the corresponding salts containing the corresponding radioactive metallic isotope in a association with hyaluronic acid esters disclosed in U.S. Pat. No. 4,851,521, we incorporate herewith by reference, and or the autocrosslinked hyaluronic acid derivatives disclosed in U.S. Pat. No. 5,676,964 we incorporated herewith by reference, for the in vivo diagnosis and for the treatment of malignant tumours. In fact they may be used in diagnostic method either alone or more preferably in association with known radioactive or non radioactive contrast media, the latter ones being activated with energy.

The diagnostic methods in question include NMR, ultrasounds and X-rays, scintigraphy, PET, etc., in which the above derivatives can be used possibly in association with paramagnetic agents such as magnetite, with non-ionic contrast agents or with radioactive isotopes such as $TC^{99m}$, Indium.

Example for the Preparation of Succinic Acid Hemiester with Hyaluronic Acid Having the Repeating Unit (I)

EXAMPLE 1

A solution of sodium hyaluronate (HA-Na, 1 g, MW 160,000) in distilled water (35 ml) and N,N-dimethylformamide (DMF, 100 ml) was stirred for ten minutes in the presence of ion exchange resin (3 G, IR 120 H +), after which the resin was removed by filtration after further dilution with DMF (100 ml). The solution was then neutralized with an excess of pyridine (10 ml) to give the pyridine salt of hyaluronic acid (HA-Py). The viscous solution was then carefully evaporated in a vacuum to remove the water present, taking care not to allow the total volume of solution to drop below about 100 ml. This procedure was repeated three times, each time adding DMF (20 ml). The solution was then treated with succinic anhydride (3 g) and pyridine (10 ml) while being stirred at room temperature for 24 hours. The reaction mixture was then concentrated, gathered with distilled water (20 ml), dialized against distilled water (13 times 750 ml) and freeze-dried to give hyaluronic acid succinylate (930 mg). Table 1 shows the assignment of the chemical shift values of the $^{13}$C.n.m.r. (50.3 MHz) spectrum of sample 1.

TABLE 1

| Chemical shift in δ ppm | non-modified HA | modified HA | other groups |
| --- | --- | --- | --- |
| 101.49 | N-1 | | |
| 55.19 | N-2 | | |
| 83.30 | N-3 | | |
| 69.30 | N-4 | | |
| 76.23 | N-5 | | |
| 61.99 | N-6 | | |
| 103.82 | G-1 | | |
| 73.21 | G-2 | | |
| 79.98 | G-3 | | |
| 80.81 | G-4 | | |
| 76.23 | G-5 | | |
| 173.84 | G-6 | | |
| 175.63 | N=C=O | | |
| 102.50 | | N-1 | |
| 83.00 | | N-3 | |
| 73.85 | | N-5 | |
| 64.08 | | N-6 | |
| 71.74 | | G-2 | |
| 29.79, 29.91 | | | CH$_2$ succinate |
| 175.35, 177.71 | | | C=O succinate |

N.M.R. Analysis shows a degree of succinylation on carbon 6 of the N-acetylglucosamine (N-6) of 0.2 (mol of succinic acid/mol of repeating unit of the polymer).

EXAMPLE 2

A solution of sodium hyaluronate (HA-Na, 1 g, MW 30,0000 in distilled water (35 ml, and N,N-dimethylformamide (DMF, 100 ml) was stirred in the presence of ion exchange resin (3 g, IR 120 H+) for 10 minutes and then the resin was removed by filtration after further dilution with DMF (100 ml). The solution was then neutralized with an excess of pyridine (10 ml) to give the pyridine salt of hyaluronic acid (HA-Py). The viscoue solution was then carefully evaporated in a vacuum to remove the water present, without allowing the total volume of the solution to drop below about 100 ml. This water-removing procedure was repeated three times, each time with the addition of DMF (20 ml). The solution was then treated with succinic anhydride (3 g) and pyridine (10 ml) while being stirred at 70° C. for 24 hours. The reaction mixture was then concentrated, gathered with distilled water (20 ml), dialized against distilled water (3 times 750 ml) and freeze-dried to give hyaluronic acid succinylate (900 mg).

Table 2 reports the assignment of the chemical shift values of the $^{13}$C;n.m.r. spectrum (50.3 MHz) of sample 2).

TABLE 2

| Chemical shift in δ ppm | non-modified HA | modified HA | other groups |
| --- | --- | --- | --- |
| 101.77 | N-1 | | |
| 54.33 | N-2 | | |
| 82.91 | N-3 | | |
| 69.93 | N-4 | | |
| 76.31 | N-5 | | |
| 60.95 | N-6 | | |
| 102.77 | G-1 | | |
| 72.58 | G-2 | | |
| 73.88 | G-3 | | |
| 80.94 | G-4 | | |
| 74.13 | G-5 | | |
| 170.00 | G-6 | | |
| 171.83 | N=C=O | | |
| 102.50 | | N-1 | |
| 83.00 | | N-3 | |
| 73.85 | | N-5 | |
| 63.36 | | N-6 | |
| 70.73 | | G-2 | |
| 28.79 | | | CH$_2$ succinate |
| 168.98, 173.00 | | | C=O succinate |

N.M.R. analysis gives a degree of succinylation on carbon 6 of the Nacetylglucosamine (N-6) of about 0.45 (mol of succinic acid/mol of repeating unit.

EXAMPLE 3

A solution of sodium hyaluronate (HA-Na, 0.5 g, MW 160,000) in distilled water (35 ml) and N,N-dimethylformamide (DMF 100 ml) was stirred in the presence of ion exchange resin (3 G, IR 120 H+) for 10 minutes and then the resin was removed by filtration after further dilution with DMF (75 ml). The solution was then neutralized with an excess of pyridine (6 ml) to give the pyridine salt of hyaluronic acid (HA-Py). the viscous solution was then carefully evaporated in a vacuum to remove the water present, without allowing the total volume of the solution to drop below about 50 ml. This water-removing procedure was repeated three times, each time with the addition of DMF (10 ml). The solution was then treated with succinic anhydride (2 g), 4-dimethylaminopyridine (10 mg) and pyridine (10 ml), while stirring at 70° C. for 46 hours. Further quantities of succinic anhydride were added (1 g) and pyridine (2.5 ml) and the mixture was stirred for another 24 hours. The reaction mixture was then concentrated, gathered with distilled water (20 ml), dialized against distilled water (3 times 750 ml) for 3 days and freeze-dried to give hyaluronic acid succinylate (450 mg). The product was characterized by a high degree of viscosity when dissolved in water, the n.m.r. spectrum in particular was characterized by wide peaks due to the sample's high degree of viscosity. The degree of modification was assessed by potentiometric assay, and proved to be 1.8 (mol of succinic acid/mol of repeating unit).

EXAMPLE 4

A solution of sodium hyaluronate (HA-NA, 0.5 g, MW 240,000) in distilled water (60 ml) and N,N-dimethylformamide (DMF 60 ml) was stirred in the presence of ion exchange resin (1 G, IR 120 H+) for 10 minutes, after which the resin was removed by filtration after further dilation with DMF (50 ml). the solution was then neutralized with an excess of pyridine (6 L) to give the pyridine salt of hyaluronic acid HA-Py). The viscous solution was then carefully evaporated in a vacuum to remove the water present, without allowing the total volume of the solution to drop below about 100 ml. This water-removing procedure was repeated three times, each time with the addition of DMF (20 ml). The gelatin like solution was then treated with succinic anhydride (2 g) and pyridine (5 ml) at 70° C. while being stirred for 18 hours. Further quantities of succinic anhydride (2.5 g) and 4- dimethylaminopyridine (200 mg) were added and the mixture was stirred for another 24 hours. The reaction mixture was then concentrated, gathered with distilled water (20 ml) and freeze-dried to give hyaluronic acid succinylate (450 mg). The product is characterized by being highly viscous when dissolved in water, the n.m.r. spectrum in particular is characterized by very wide peaks due to the highly viscous character of the samples. The degree of modification was assessed by potentiometric assay and the result was 2.5 (mol of succinic acid/mol of repeating unit).

EXAMPLE 5

A solution of sodium hyaluronate (HA-Na, 1 g, MW 40,000) in distilled water (60 ml) and N,N-dimethylformamide (DMF 60 ml) was stirred in the presence of ion exchange resin (1 g, IR 120 H+) for 10 minutes, after which the resin was removed by filtration after further dilution with DMF (50 ml). The solution was then neutralized with an excess of pyridine (10 ml) to give the pyridine salt of hyaluronic acid (HA-Py). The viscous solution was then carefully evaporated in a vacuum to remove the water present, without allowing the total volume of the solution to drop below 50 ml. This water-removing procedure was repeated three times, each time with the addition of DMF (20 ml). The solution was then treated with succinic anhydride (3 g) and pyridine (10 ml) at 70° C. while stirring for 18 hours. Further quantities of succinic anhydride (2.5 g) and 4dimehylaminopyridine (200 mg) were added and the mixture was stirred for another 24 hours. The reaction mixture, which was brown in colour, was then concentrated, gathered with distilled water (20 ml), dialized against distilled water (3 times 750 ml) and freeze-dried to give hyaluronic acid succinylate (850 mg). The degree of succinylation was assessed by potentiometric assay and was 3.5 (mol of succinic acid/mol of repeating unit).

EXAMPLE 6

A solution of sodium hyaluronate (HA-Na, 0.5 g, Mw 760,000) in distilled water (60 ml) and N,N-dimethylformamide (DMG 60 ml) was stirred in the presence of ion exchange resin (1 g, IR 120 H+) for 10 minutes, after which the resin was removed by filtration after further dilution with DMF (50 ml). The solution was then neutralized with an excess of pyridine (6 ml) to give the pyridine salt of hyaluronic acid (HA-Py). The viscous solution was then carefully evaporated to remove the water present, without allowing the total volume of solution to drop below about 50 ml. This procedure was repeated three times, each time with the addition of DMF (20 ml). The gelatin-like solution was then treated with succinic anhydride (2 g) and 4-dimethylaminopyridine (200 mg) and the mixture was stirred for another 24 hours. The reaction mixture was then concentrated, gathered with distilled water (20 ml), dialized against distilled water (3 times 750 ml) and freeze-dried dried to give hyaluronic acid succinylate (430 mg). The product is characterized by being highly viscous when dissolved in water, the n.m.r. spectrum in particular is characterized by very wide peaks due to the highly viscous character of the samples. The degree of modification was assessed by potentiometric assay and was 2.5 (mol of succinic acid/mol of repeating unit).

Examples of the Preparation of Silver Salts of O-succinyl Hyaluronate

EXAMPLE 7

100 mg of O-succinyl hyaluronate, prepared as described in Example 1 were dissolved in 10 ml of distilled water. The polymer solution was then supplemented with 10 ml of a solution of $AgNO_3$ 1N. The white precipitate thus formed was kept in suspension while being stirred constantly for two hours, and was then gathered by filtration through a Buchner funnel, washed several times with ethanol and dried in a vacuum oven set at 40° C. All these operations were performed in the dark to avoid the formation of silver oxide. Atomic absorption analysis showed a silver content of 23.5% in weight, equal to 87% of the theoretical stoichiometric value.

EXAMPLE 8

70 mg of hyaluronic acid succinylate, prepared as described in Example 3 were dissolved in 14 ml of distilled water. The polymer solution, which was highly viscous, was supplemented with 14 ml of a solution of $AgNO_3$ 1N. A grey precipitate formed immediately and was kept in suspension while being constantly stirred for two hours, after which it was gathered by filtration through a Buchner funnel. It was washed several times with ethanol and dried in a vacuum oven set at 40° C. All these operations were performed in the dark to avoid the formation of silver oxide. Atomic absorption analysis showed the silver content to be 27% in weight, equal to 71% of the theoretical stoichiometric value.

EXAMPLE 9

100 mg of hyaluronic acid succinylate, prepared as described in Example 4, were dissolved in 20 ml of distilled water. The polymer solution, which was highly viscous, was supplemented with 20 ml of a solution of $AgNO_3$ 2N. A white precipitate formed immediately and was kept in suspension while being constantly stirred for two hours. It was then recovered by filtration through a Buchner funnel, washed several times with ethanol and dried in a vacuum oven set at 40° C. All these operations were performed in the dark to avoid the formation of silver oxide. Atomic absorption analysis showed the silver content to be 28.8% in weight, equal to 70.5% of the theoretical stoichiometric value.

EXAMPLE 10

100 mg of hyaluronic acid succinylate, prepared as described in Example 5, were dissolved in 10 ml of distilled water. The polymer solution, which was highly viscous, was supplemented with 10 ml of a solution of $AgNO_3$ 2N. A brownish precipitate formed immediately and was kept in suspension while being constantly stirred for two hours, after which it was recovered by filtration through a Buchner funnel, washed several times with ethanol and dried in a vacuum oven at 40° C. All these operations were performed in the dark to avoid the formation of silver oxide. Atomic absorption analysis showed the silver content to be 31%, equal to 70.2% of the theoretical stoichiometric value.

EXAMPLE 11

100 mg of hyaluronic acid succinylate, prepared as described in Example 6, were dissolved in 10 ml of distilled water. The polymer solution, which was highly viscous, was supplemented with 10 ml of a solution of $AgNO_3$ 1N. A brownish precipitate was immediately formed, which was kept in suspension while being constantly stirred for two hours, after which it was recovered by filtration through a Buchner funnel, washed several times with ethanol and dried in a vacuum oven set at 40° C. All these operations were performed in the dark to avoid the formation of silver oxide. Atomic absorption analysis showed the silver content to be 27% in weight, equal to 71% of the theoretical stoichiometric value.

Examples of the Preparation of Zinc Salts of Hyaluronic Acid Succinylate

EXAMPLE 12

100 mg of hyaluronic acid succinylate, prepared as described in Example 1 were dissolved in 10 ml of distilled water. The polymer solution was then supplemented with 10 ml of a solution of $ZnCl_2$ 0.2 N. The solution was stirred constantly for 2 hours, after which 3 volumes of ethanol were added to precipitate the soluble zinc salt. The precipitate was recovered by centrifugation at 3,000 rpm for 15 minutes, washed several times with ethanol and dried in a vacuum oven set at 40° C. Atomic absorption analysis showed a zinc content of 10%, equal to 101% of the theoretical stoichiometric value.

EXAMPLE 13

100 mg of hyaluronic acid succinylate prepared as described in Example 3 were dissolved in 20 ml of distilled water. The polymer solution, which was highly viscous, was supplemented with 20 ml of a solution of $ZnCl_2$ 2 N. After the addition of zinc salt, a powdery precipitate was formed, which was recovered by centrifugation at 3,000 rpm for 15 minutes, washed several times with ethanol and dried in a vacuum oven set at 40° C. Atomic absorption analysis showed the zinc content in the sample to be 15.3% equal to 105% of the theoretical stoichiometric value.

EXAMPLE 14

100 mg of hyaluronic acid succinylate prepared as described in Example 4 were dissolved in 20 ml of distilled water. The polymer solution, which was highly viscous, was supplemented with 20 ml of a solution of $ZnCl_2$ 2N. After the addition of zinc salt, a powdery precipitate was formed which was recovered by centrifugation at 3,000 rpm for 15 minutes, washed several times With ethanol and dried in a vacuum oven set at 40° C. Atomic absorption analysis showed the zinc content of the sample to be 17.7% in weight, equal to 105% of the theoretical stoichiometric value.

Example of the Preparation of the Copper Salt of Hyaluronic Acid Succinylate

EXAMPLE 15

100 mg of hyaluronic acid succinylate prepared as described in Example 5 were dissolved in 10 ml of distilled water. The polymer solution was then supplemented with 10 ml of a solution of $CuCl_2$ 2N. After the addition of copper salt a blue precipitate was formed which was recovered by centrifugation at 3,000 rpm for 15 minutes, washed several times with ethanol and dried in a vacuum oven set at 40° C. Atomic absorption analysis showed the copper content of the sample to be 21.4% in weight, equal to 110% of the theoretical stoichiometric value. It is therefore probable that a small amount of copper salt is incorporated by the polymer during precipitation of the derivative.

Example of the Preparation of Gold Salt of Hyaluronic Acid Succinylate

EXAMPLE 16

100 mg of hyaluronic acid succinylate prepared as described in Example 3 were dissolved in 20 ml of distilled water. The polymer solution, which was highly viscous, was then supplemented with 20 ml of a solution of $HAuCL_4$ 0.5N. After addition of gold salt, a precipitate was formed which was recovered by centrifugation at 3,000 rpm for 15 minutes, washed several times with ethanol and dried in a vacuum oven at 40° C. The gold content in the sample proved to be 13% in weight, equal to 44% of the theoretical stoichiometric value.

Example of the Preparation of Iron Salts of Hyaluronic Succinylate

EXAMPLE 17

A solution of sodium hyaluronate (HA-Na, 0.5 g, MW 160,000) in distilled water (35 ml) and N,N-Dimethilformamide (DMF 100 ml) is stirred in the presence of ion exchange resin (3 g, IR 120 H+) for 10 minutes and then the resin is removed by filtration after further dilution with DMF (75 ml). The solution is then neutralized with an excess of pyridine (6 ml) to give the pyridine salt of hyaluronic acid (HA-Py), the viscous solution is then carefully evaporated in a vacuum to remove the water present, without allowing the total volume of the solution to drop below about 50 ml. This water removing procedure is repeated three times, each time with the addition of DMF (10 ml). The solution is then treated with succinic anhydride (2 g), 4-dimethylaminopyridine (10 mg) and pyridine (10 ml), while stirring at 70° C. for 48 hours. Further quantities of succinic anhydride are added (1 g) and pyridine (2.5 ml) and the mixture is stirred for another 24 hours. The reaction mixture is then concentrated, gathered with distilled water (20 ml), dialized against distilled water (3 times 750 ml) for 3 days and freeze-dried to give hyaluronic acid succinylate (450 mg). Hyaluronic acid succinylate thus obtained is dissolved in 90 ml of distilled water. The polymer solution, which is highly viscous, is supplemented with 90 ml of a solution of $FeCl_2$ 1N. A white precipitate forms immediately and is kept in suspension while being constantly stirred for two hours, after which it is gathered by filtration through a buchner funnel. It is washed several times with ethanol and dried in a vacuum oven set at 40° C. Atomic absorption analysis show the iron content to be 9.8% in weigth, equal to 80% of the theoretical stoichiometric value.

We claim:
1. Succinic acid hemiester of hyaluronic acid, or of a hyaluronic acid partial or total ester, said succinic hemiester having the following repeating unit (I):

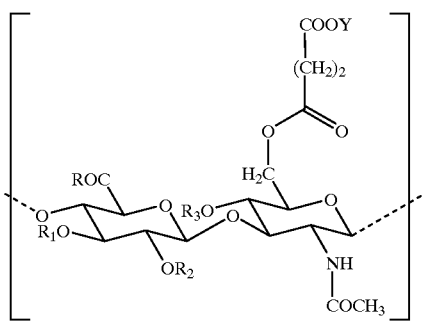

(I)

wherein $R_1$, $R_2$ and $R_3$ have the same or different meanings selected from the group consisting of H and CO—$(CH_2)_2$—COOY, wherein Y is H, R is OH, or R is an alcoholic residue.

2. The succinic acid hemiester according to claim 1 wherein in the repeating unit (I) $R_1=R_2=R_3=H$.

3. The succinic acid hemiester according to claim 1 having at least one repeating unit (I) wherein $R_1=R_3=H$ and $R_2=CO$—$(CH_2)_2$—COOY and at least one repeating unit (I), wherein $R_2=R_3=H$, and $R_1=CO$—$(CH_2)_2$—COOY.

4. Heavy metal salt of succinic acid hemiester with hyaluronic acid or with a hyaluronic acid total or partial ester, said salt having the following repeating unit (II):

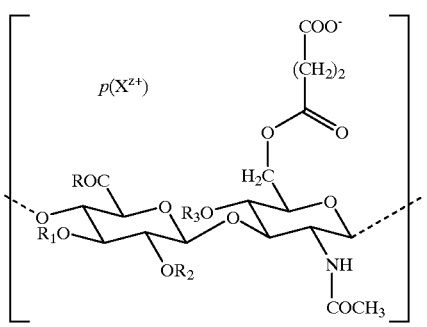

(II)

wherein $R_1$, $R_2$ and $R_3$ have the same or different meanings selected from the group consisting of H and CO—$(CH_2)_2$—COO$^-$, R is O$^-$ or R is an alcoholic residue, ($X^{z+}$) is a cation of a heavy metal in which z is a number between 1 and 6, p is an integer or a decimal number between 0.1 and 5, provided that p($X^{z+}$) is equal to the number of anionic groups COO$^-$ present in said repeating unit.

5. A diagnostical composition for the diagnosis of tumours containing the heavy metal salt according to claim 4, either as a contrast medium or in association with a known non radioactive contrast medium.

6. An antitumoral composition containing the heavy metal salts according to claim 4, optionally in association with known radioactive or non radioactive antitumoral agents.

7. Cosmetic creams and ointments containing at least one heavy metal salt of succinic acid hemiester with hyaluronic acid or a hyaluronic acid total or partial ester according to claim 4.

8. Shave and after-shave lotions containing at least one heavy metal salt of succinic acid hemiester with hyaluronic acid or a hyaluronic acid total or partial ester according to claim 4.

9. Hair lotions containing at least one heavy metal salt of succinic acid hemiester with hyaluronic acid or a hyaluronic acid total or partial ester according to claim 4.

10. Membranes containing at least one heavy metal salt of succinic acid hemiester with hyaluronic acid or a hyaluronic acid total or partial ester according to claim 4.

11. Non-woven tissues containing at least one heavy metal salt of succinic acid hemiester with hyaluronic acid or a hyaluronic acid total or partial ester according to claim 4.

12. Gauze containing at least one heavy metal salt of succinic acid hemiester with hyaluronic acid or a hyaluronic acid total or partial ester according to claim 4.

13. The heavy metal salt according to claim 4 wherein X is selected from the group consisting of Ag, Cu, Zn, Au, Ce, W, Fe.

14. The heavy metal salt according to claim 4, wherein $R_1=R_2=R_3=H$ and X is selected from the group consisting of Ag, Au, Cu, Zn and Fe, z is between 1 and 3 and p is between 0.3 and 2.

15. The heavy metal salt according to claim 4, having at least one repeating unit (II) wherein $R_1=R_3=H$ and $R_2=CO$—$(CH_2)_2$—COO$^-$, and at least one repeating unit (II) wherein $R_2=R_3=H$ and $R_1=CO$—$(CH_2)_2$—COO$^-$, X is selected from the group consisting of Ag, Au, Cu, Zn and Fe, z is between 1 and 3 and p is between 0.6 and 3.

16. A process for preparing the heavy metal salt of succinic acid hemiester with hyaluronic acid or with a partial ester of hyaluronic acid, said salt having the following repeating unit (II):

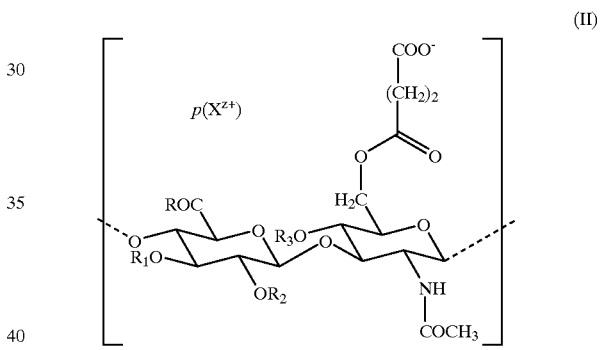

(II)

wherein $R_1$, $R_2$ and $R_3$ have the same or different meanings selected from the group consisting of H and CO—$(CH_2)_2$—COO$^-$, R is O$^-$ or R is an alcoholic residue, ($X^{z+}$) is a cation of a heavy metal in which z is a number between 1 and 6, p is an integer or a decimal number between 0.1 and 5, selected from the group consisting of Ag, Cu, Zn, Au, Ce, W and Fe, provided that p($X^{z+}$) is equal to the number of anionic groups COO$^-$ present in said repeating unit, and provided that at least in one repeating unit (II) R is OH, said process comprising the following steps:

a) reacting the hyaluronic acid sodium salt into a hyaluronic acid salt with a compound selected from the group consisting of pyridine, a tetraalkylammonium salt, a tetraarylammonium salt, a tetraalkylphosphonium salt and a tetraarylphosphonium salt, in the presence of water and an aprotic solvent, thereby obtaining the corresponding pyridinium, tetraalkylammonium, tetraarylammonium, tetraalkylphosphonium and tetraarylphosphonium hyaluronate, b) treating the solution coming from step a) with succinic anhydride in the presence of an organic base, as a catalyst, removing the pyridinium, tetraalkylammonium, tetraarylammonium, tetraalkylphosphonium or tetraarylphosphonium cation by dialysis, thereby obtaining the succinic acid hemiester with hyaluronic acid or a partial ester thereof, said hemiester having at least one repeating unit (I):

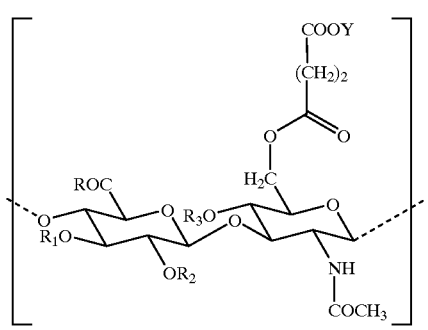

wherein $R_1$, $R_2$ and $R_3$ have the same or different meanings selected from the group consisting of H and CO—$(CH_2)_2$—COOY, wherein Y is H, R is OH, or R is an alcoholic residue, provided that at least in one repeating unit (I) R is OH, and optionally recovering said succinic acid hemiester with hyaluronic acid or a partial ester thereof as a solid product by freeze-drying, c) treating the solution directly coming from step b), or an aqueous solution of said recovered solid product coming from step b), with an aqueous solution of an inorganic salt of the heavy metal, thereby obtaining the heavy metal salt of succinic acid hemiester with hyaluronic acid or with a partial ester of hyaluronic acid, and recovering said salt by filtration and vacuum drying.

17. The process according to claim 16, wherein in step a) the hyaluronic acid sodium salt is converted to said hyaluronic acid pyridinium salt by using the following operating conditions:

i) dissolving said hyaluronic acid sodium salt in a mixture of water and dimethylformamide,
ii) treating the solution coming from step i) with a cationic exchange resin to obtain free hyaluronic acid,
iii) neutralizing the reaction mixture with pyridine, thereby obtaining said hyaluronic acid pyridinium salt.

18. The process according to claim 16, wherein step b) is carried out at 70° C. wherein the ratio of moles of succinic anhydride to moles of total free OH groups present in the following repeating unit (III) of the starting hyaluronic acid or hyaluronic acid partial ester is from 15:1 to 90:1:

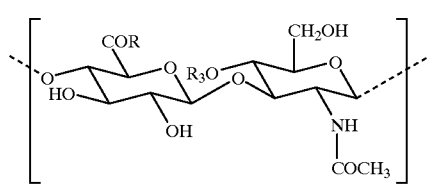

wherein $R_3$ is selected from the group consisting of H and CO—$(CH_2)_2$—COOY, and Y is H, R is OH or R is an alcoholic residue, provided that at least in one repeating unit R is OH, in the presence of a catalyst selected from the group consisting of 4-dimethylaminopyridine, pyridine, and mixtures thereof.

19. The process according to claim 16, for preparing Ag salts of the succinic acid hemiester with hyaluronic acid or with a hyaluronic acid partial ester wherein in step (c) the succinic acid hemiester with hyaluronic acid or the succinic acid hemiester with a hyaluronic acid partial ester is treated with an aqueous solution of silver nitrate.

20. The process according to claim 16, for preparing Zn salts of the succinic acid hemiester with hyaluronic acid or with a hyaluronic acid partial ester wherein in step (c) the succinic acid hemiester with hyaluronic acid or with hyaluronic acid partial ester is treated with an aqueous solution of $ZnCl_2$.

21. The process according to claim 16, for preparing Cu salts of the succinic acid hemiester with hyaluronic acid or with a hyaluronic acid partial ester wherein in step (c) the succinic acid hemiester with hyaluronic acid or the succinic acid hemiester with hyaluronic acid partial ester is treated with an aqueous solution of $CuCl_2$.

22. The process according to claim 16, for preparing Au salts of the succinic acid hemiester with hyaluronic acid or with a hyaluronic acid partial ester, wherein in step (c) the succinic acid hemiester with hyaluronic acid or the succinic acid hemiester with hyaluronic acid partial ester is treated with an aqueous solution of $HAuCl_4$.

23. The process according to claim 16, for preparing Fe salts of the succinic acid hemiester with hyaluronic acid or with a hyaluronic acid partial ester, wherein in step (c) the succinic acid hemiester with hyaluronic acid or with a hyaluronic acid partial ester is treated with an aqueous solution of $FeCl_2$.

24. A process for preparing a heavy metal salt of succinic acid hemiester with a hyaluronic acid total ester, said salt having the following repeating unit (II):

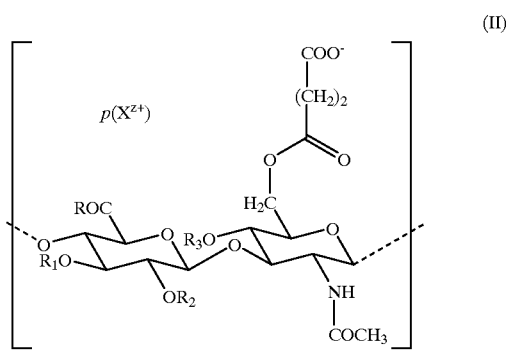

wherein $R_1$, $R_2$, and $R_3$ have the same or different meanings selected from the group consisting of H and CO—$(CH_2)_2$—COO$^-$, R is an alcoholic residue, ($X^{z+}$) is a cation of a heavy metal in which z is a number between 1 and 6, p is an integer or a decimal number between 0.1 and 5, selected from the group consisting of Ag, Cu, Zn, Au, Ce, W and Fe, provided that p($X^{z+}$) is equal to the number of anionic groups COO$^-$ present in said repeating unit, said process comprising the following steps:

b') treating hyaluronic acid total ester dissolved or suspended in a mixture of water and an aprotic solvent with succinic anhydride in the presence of an organic base, thereby obtaining said succinic acid hemiester with a hyaluronic acid total ester, said hemiester having the repeating unit (I):

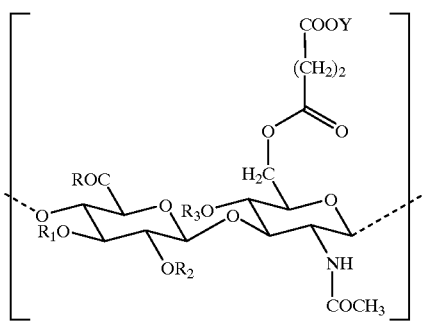

(I)

wherein $R_1$, $R_2$ and $R_3$ have the same or different meanings selected from the group consisting of H and CO—$(CH_2)_2$—COOY, wherein Y is H, and R is a residue of an alcohol, and optionally recovering succinic acid hemiester with a hyaluronic acid total ester as a solid product by freeze-drying.

c') treating the solution directly coming from step b'), or an aqueous solution of said recovered solid product coming from step b'), with an aqueous solution of an inorganic salt of a heavy metal, thereby obtaining the heavy metal salt of succinic acid hemiester with hyaluronic acid total ester, and recovering said salt by filtration and vacuum drying.

25. The process according to claim 24, wherein step b') is carried out at 70° C., wherein the ratio of moles of succinic anhydride to total free OH groups present in the following repeating unit (III) of the starting hyaluronic acid total ester is from 15.1: to 90:1:

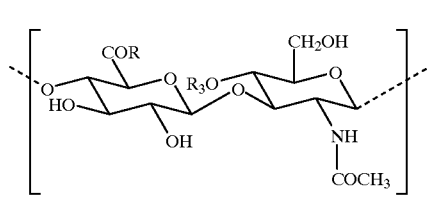

(III)

wherein $R_3$ is selected from the group consisting of H and CO—$(CH_2)_2$—COOY and Y is H, and R is an alcoholic residue in the presence of a catalyst selected from the group consisting of 4-dimethylpyridine, pyridine, and mixtures thereof.

26. The process according to claim 24, for preparing Ag salts of the succinic acid hemiester with a hyaluronic acid total ester wherein in step c') the succinic acid hemiester with a hyaluronic acid total ester is treated with an aqueous solution of silver nitrate.

27. The process according to claim 24, for preparing Zn salts of the succinic acid hemiester with a hyaluronic acid total ester wherein in step c') the succinic acid hemiester with a hyaluronic acid total ester is treated with an aqueous solution of $ZnCl_2$.

28. The process according to claim 24, for preparing Cu salts of the succinic acid hemiester with a hyaluronic acid total ester wherein in step c') the succinic acid hemiester with a hyaluronic acid total ester is treated with an aqueous solution of $CuCl_2$.

29. The process according to claim 24, for preparing Au salts of the succinic acid hemiester with a hyaluronic acid total ester wherein in step c') the succinic acid hemiester with a hyaluronic acid total ester is treated with an aqueous solution of $HAuCl_4$.

30. The process according to claim 24, for preparing Fe salts of the succinic acid hemiester with a hyaluronic acid total ester wherein in step c') the succinic acid hemiester with a hyaluronic acid total ester is treated with an aqueous solution of $FeCl_2$.

31. A therapeutic composition containing as an active ingredient at least one heavy metal salt of succinic acid hemiester with hyaluronic acid or with a hyaluronic acid total or partial ester, said salt having the following repeating unit (II):

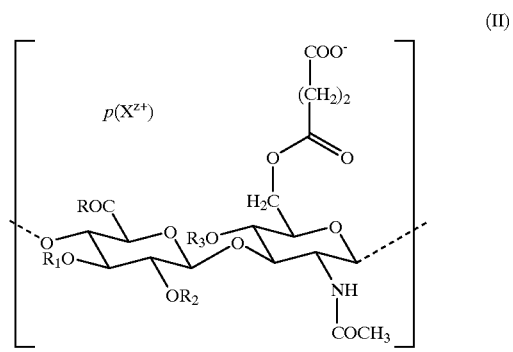

(II)

wherein $R_1$, $R_2$ and $R_3$ have the same or different meanings selected from the group consisting of H and CO—$(CH_2)_2$—COO$^-$, R is O$^-$ or R is an alcoholic residue, $(X^{z+})$ is a cation of a heavy metal in which z is a number between 1 and 6, p is an integer or a decimal number between 0.1 and 5, provided that $p(X^{z+})$ is equal to the number of anionic groups COO$^-$ present in said repeating unit, optionally in association with other active ingredients.

32. The therapeutic composition according to claim 31, in the form of an ointment, cream or gel.

33. The therapeutic composition according to claim 31, containing as the active ingredient an Ag salt of a succinic acid hemiester with hyaluronic acid or with a hyaluronic acid total or partial ester.

34. The therapeutic composition according to claim 31, containing as the active ingredient at least one heavy metal salt of succinic acid hemiester with hyaluronic acid or with a hyaluronic acid partial or total ester, selected from the group consisting of salts of Au, Cu, Zn, Fe, and mixtures thereof.

35. A heavy metal salt of succinic acid hemiester with hyaluronic acid or with a hyaluronic acid total or partial ester, said salt having the following repeating unit (II):

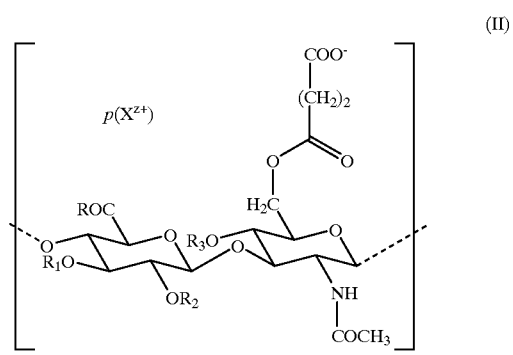

(II)

wherein $R_1$, $R_2$ and R have the same or different meanings selected from the group consisting of H and CO—$(CH_2)_2$—COO$^-$, R is O$^-$ or R is an alcoholic residue, $(X^{z+})$ is a cation of a heavy metal in which z is a number between 1 and 6, p is an integer or a decimal number between 0.1 and 5, provided that $p(X^{z+})$ is equal to the number of anionic groups COO⁻ present in said repeating unit, wherein said heavy metal is a radioactive isotope.

36. A diagnostic composition for the in vivo diagnosis of tumours according to claim 35, containing the heavy metal salt either as a contrast medium or in association with a known radioactive or a non-radioactive contrast medium.

37. An antitumoral composition containing the heavy metal salts according to claim 35, optionally in association with known radioactive or non radioactive antitumoral agents.

* * * * *